(12) United States Patent
Yanagisawa et al.

(10) Patent No.: US 6,777,700 B2
(45) Date of Patent: Aug. 17, 2004

(54) PARTICLE BEAM IRRADIATION SYSTEM AND METHOD OF ADJUSTING IRRADIATION APPARATUS

(75) Inventors: Masaki Yanagisawa, Hitachi (JP); Hiroshi Akiyama, Hitachiohta (JP); Koji Matsuda, Hitachi (JP); Hisataka Fujimaki, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/455,497

(22) Filed: Jun. 6, 2003

(65) Prior Publication Data

US 2004/0000650 A1 Jan. 1, 2004

(30) Foreign Application Priority Data

Jun. 12, 2002 (JP) ........................................ 2002-170778

(51) Int. Cl.[7] ................................................ H05H 9/00
(52) U.S. Cl. .................... 250/492.3; 315/501; 315/505; 315/507
(58) Field of Search ...................... 250/492.3; 315/501, 315/505, 507

(56) References Cited

U.S. PATENT DOCUMENTS

| | | | |
|---|---|---|---|
| 5,039,867 A | | 8/1991 | Nishihara et al. |
| 5,969,367 A | * | 10/1999 | Hiramoto et al. ......... 250/492.3 |
| 6,265,837 B1 | * | 7/2001 | Akiyama et al. ........... 315/503 |
| 6,316,776 B1 | * | 11/2001 | Hiramoto et al. ......... 250/492.3 |
| 6,597,005 B1 | * | 7/2003 | Badura et al. ............ 250/505.1 |
| 6,617,598 B1 | * | 9/2003 | Matsuda ................... 250/492.3 |

FOREIGN PATENT DOCUMENTS

| | | |
|---|---|---|
| DE | 199 07 098 A1 | 8/2000 |
| EP | 0 779 081 | 6/1997 |
| EP | 826 394 A2 | 3/1998 |
| EP | 1 041 579 A1 | 10/2000 |
| JP | 10-199700 | 7/1998 |
| JP | 10-211292 | 8/1998 |
| JP | 2000-202047 | 7/2000 |

* cited by examiner

Primary Examiner—John R. Lee
Assistant Examiner—Paul M. Gurzo
(74) Attorney, Agent, or Firm—Dickstein Shapiro Morin & Oshinsky LLP

(57) ABSTRACT

The present invention provides an increased degree of uniformity of radiation dose distribution for the interior of a diseased part. A particle beam therapy system includes a charged particle beam generation apparatus and an irradiation apparatus. An ion beam is generated by the charged particle beam generation apparatus. The irradiation apparatus exposes a diseased part to the generated ion beam. A scattering device, a range adjustment device, and a Bragg peak spreading device are installed upstream of a first scanning magnet and a second scanning magnet. The scattering device and the range adjustment device are combined together and moved along a beam axis, whereas the Bragg peak spreading device is moved independently along the beam axis. The scattering device moves to adjust the degree of ion beam scattering. The range adjustment device moves to adjust ion beam scatter changes caused by an absorber thickness adjustment. The Bragg peak spreading device moves to adjust ion beam scatter changes arising out of an SOBP device. These adjustments provide uniformity of radiation dose distribution for the diseased part.

24 Claims, 10 Drawing Sheets

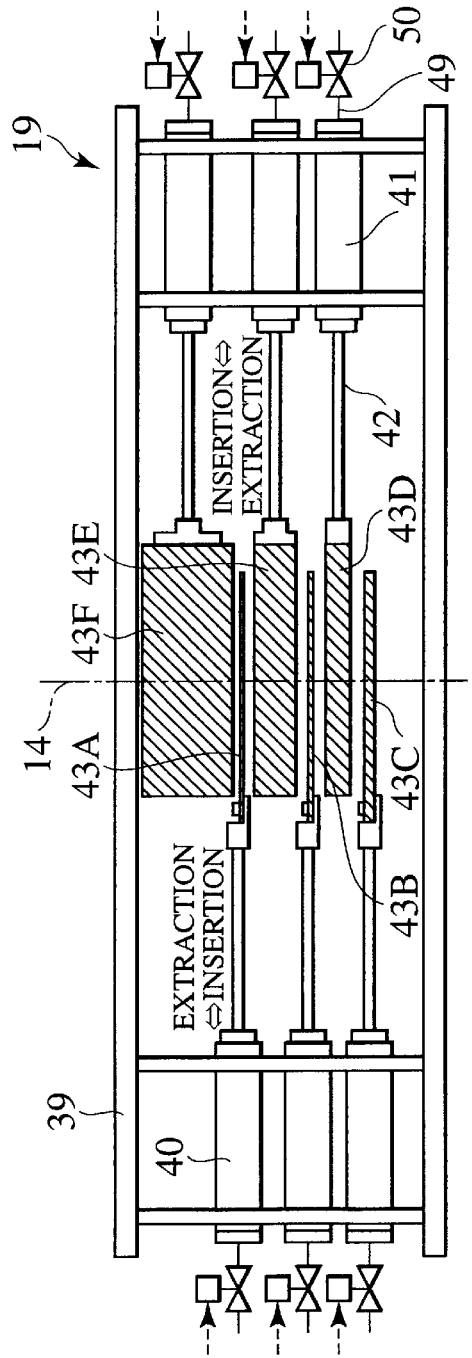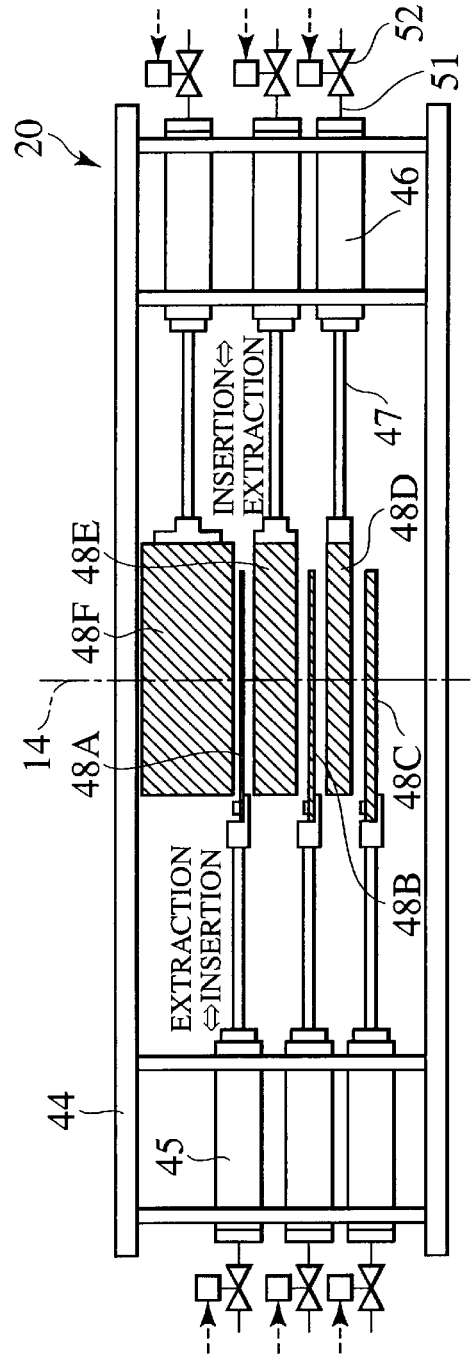

PARTICLE BEAM IRRADIATION SYSTEM AND METHOD OF ADJUSTING IRRADIATION APPARATUS

BACKGROUND OF THE INVENTION

The present invention relates to a particle beam irradiation system, and more particularly to a particle beam irradiation system for use as a particle beam therapy system for exposing a diseased part to a proton, carbon, or other charged particle beam for therapy purposes, a material irradiation system for exposing a material to a charged particle beam, a food irradiation system for exposing food to a charged particle beam, or a radioisotope production system based on a charged particle beam.

A conventional particle beam therapy system comprises a charged particle beam generation apparatus, a beam transport, and a rotary irradiation device. The charged particle beam generation apparatus includes a synchrotron (cyclotron) as an accelerator. After being accelerated to a predefined energy, a charged particle beam (hereinafter referred to as an ion beam) travels to the irradiation device via the beam transport (hereinafter referred to as the first beam transport). The rotary irradiation device includes an irradiation device beam transport (hereinafter referred to as the second beam transport), an irradiation apparatus, and a rotating device (rotary gantry) for rotating the second beam transport and irradiation apparatus as an assembly. The ion beam passes through the second beam transport and then falls on a cancerous part of a patient via the irradiation apparatus.

The irradiation apparatus shapes and emits an ion beam, which is generated by the charged particle beam generation apparatus, in accordance with the shape of a diseased part targeted for irradiation. Roughly speaking, the irradiation apparatus can be divided into three types. The first type is an irradiation apparatus based on a scatterer method. The second type is an irradiation apparatus based on a wobbling method (JP-A No. 211292/1998 and JP-A No. 202047/2000). The third type is an irradiation apparatus based on a scanning method (JP-A No. 199700/1998).

When the interior of a patient's body is to be irradiated with an ion beam emitted from the irradiation apparatus, it is desirable that the radiation dose distribution be uniform in the direction of ion beam propagation (the direction of the depth within the patient's body) and in the direction perpendicular to the direction of ion beam propagation. Such uniformity of radiation dose distribution is especially important within a cancerous area. This uniformity is desired no matter which one of the above-mentioned three types of irradiation apparatuses is used for ion beam irradiation. In a particle beam therapy system containing the aforementioned conventional irradiation apparatus, however, it has been difficult to maintain a high degree of radiation dose distribution uniformity in the direction of the depth while keeping a high radiation dose level particularly for a bulky diseased part (region targeted for irradiation).

SUMMARY OF THE INVENTION

It is therefore an object of the present invention to provide a particle beam irradiation system that is capable of increasing the uniformity of radiation dose distribution in the direction of the depth of a diseased part.

To achieve the above object, the present invention provides an irradiation apparatus in which at least either a scattering device or a Bragg peak spreading device is mounted in such a manner that the device is movable in the direction of charged particle beam propagation. Since at least either the scattering device or Bragg peak spreading device can move in the direction of charged particle beam propagation, it is possible to increase the uniformity of radiation dose distribution for the irradiation target that is exposed to a charged particle beam.

Preferably, at least one of a scattering device, a range adjustment device, and a Bragg peak spreading device is mounted in the irradiation apparatus in such a manner that the device is movable in the direction of charged particle beam propagation. Since at least either one of the scattering device, range adjustment device, and Bragg peak spreading device can move in the direction of charged particle beam propagation, it is possible to increase the uniformity of radiation dose distribution for the irradiation target that is exposed to a charged particle beam.

BRIEF DESCRIPTION OF THE DRAWINGS

Other objects and advantages of the invention will become apparent from the following description of embodiments with reference to the accompanying drawings in which:

FIG. 3 is a vertical cross-sectional view of a scattering device shown in FIG. 2;

FIG. 4 is a vertical cross-sectional view of a range adjustment device shown in FIG. 2;

DETAILED DESCRIPTION OF THE PREFERRED EMBODIMENTS

First Embodiment

Figure 1:
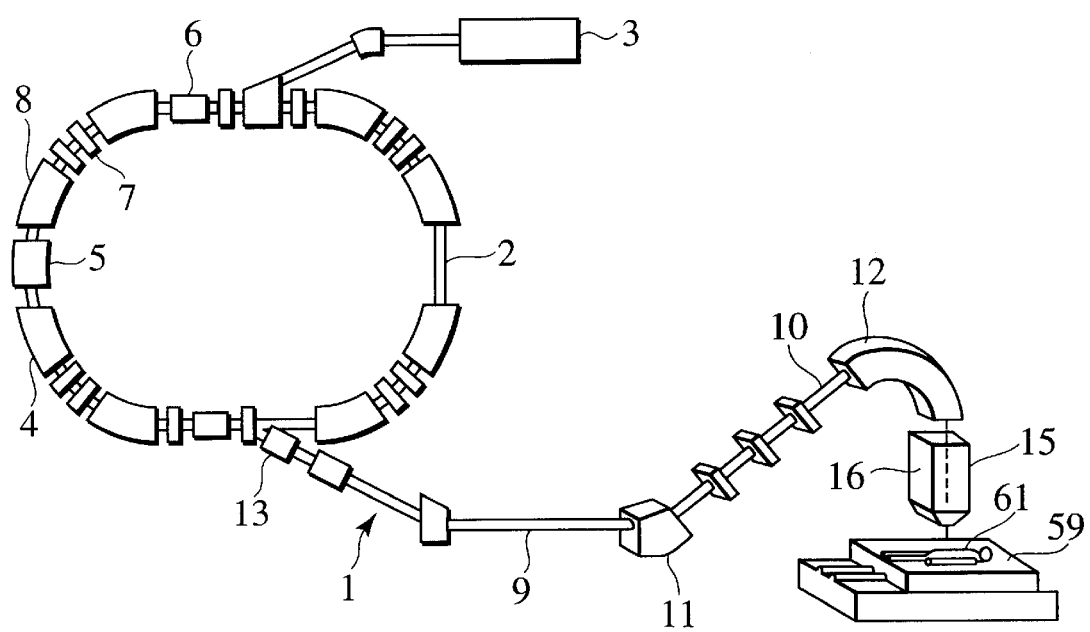
FIG. 1 illustrates the configuration of a particle beam therapy system in accordance with a first embodiment of the present invention.

A particle beam therapy system according to a preferred embodiment of the present invention will now be described with reference to FIG. 1. The particle beam therapy system 1 according to the present embodiment comprises a charged particle beam generation apparatus 2 and an irradiation apparatus 15. The charged particle beam generation apparatus 2 includes an ion source (not shown), a preaccelerator 3, and a synchrotron 4. Ions generated by the ion source (e.g., proton ions or carbon ions) are accelerated by the preaccelerator 3 (e.g., linear accelerator). An ion beam emitted from the preaccelerator 3 enters the synchrotron 4. In the synchrotron 4, the ion beam is energized and accelerated by high-frequency power, which is applied by a high-frequency acceleration cavity 5. After the energy of the ion beam circulating within the synchrotron 4 is raised to a preselected level, an outgoing high-frequency application device 6 applies a high frequency to the ion beam. Upon high-frequency application to the ion beam, which is circulating within a stability limit, the ion beam exceeds the stability limit and comes out of the synchrotron 4 via an outgoing deflector 13. When the ion beam is emitted, the electrical current induced by a four-pole magnet 7, a polarized magnet 8, and other magnets provided for the synchrotron 4 is maintained at a setting and the stability limit is maintained substantially constant. The ion beam emission from the synchrotron 4 stops at the end of high-frequency power application to the high-frequency application device 6.

The ion beam emitted from the synchrotron 4 travels through a beam transport 9 to the irradiation apparatus 15, which is an irradiation nozzle apparatus. An inverted U-shaped section 10, which is part of the beam transport 9, and the irradiation apparatus 15 are mounted in a rotary gantry (not shown). The inverted U-shaped section 10 includes polarized magnets 11, 12. The ion beam comes out of the irradiation apparatus 15 and falls on a diseased part 62 (FIG. 2) of a patient 61 who is on a patient couch (bed) 59.

Figure 2:
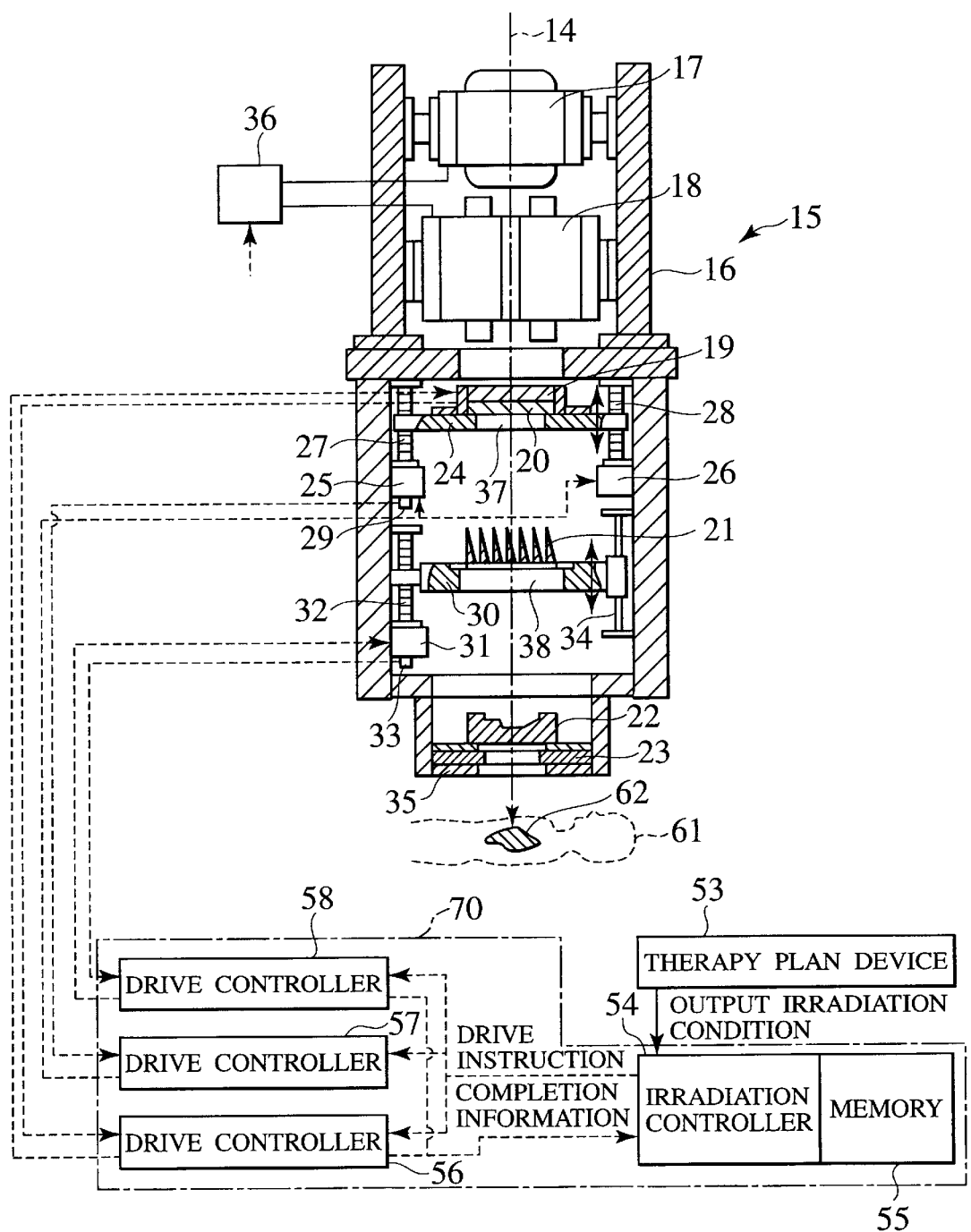
FIG. 2 is a vertical cross-sectional view of an irradiation apparatus shown in FIG. 1.

The configuration of the irradiation apparatus 15 according to the present embodiment will now be described in detail with reference to FIG. 2. The irradiation apparatus 15 is based on the wobbling method. The irradiation apparatus 15 has a casing 16, which is mounted on the inverted U-shaped section 10. From upstream to downstream of ion beam propagation, the components housed in the casing 16 are a first scanning magnet 17, a second scanning magnet 18, a scattering device 19, a range adjustment device 20, and a Bragg peak spreading device (hereinafter referred to as an SOBP device) 21. The first scanning magnet 17 and the second scanning magnet 18 are positioned upstream of the scattering device 19 and mounted on the casing 16. The scattering device 19 and the range adjustment device 20 are integral with each other and mounted on a support member 24 having a through-hole 37. The support member 24 meshes with ball screws 27, 28, which travel through two threaded holes. The upper ends of the ball screws 27, 28 are attached to the casing 16 in a rotatable manner. The lower ends of the ball screws 27, 28 are coupled to the rotating shafts of AC servomotors 25, 26, which are mounted on the casing 16. An encoder 29 is coupled to the rotating shaft of the AC servomotor 25. An alternative configuration may be employed so as to use either the AC servomotor 25 or the AC servomotor 26. Further, stepper motors may be used in place of the AC servomotors. The SOBP device 21 comprises a plurality of wedge-shaped members, which are extended toward the range adjustment device 20. Strictly speaking, both sides of the wedge-shaped members are shaped like a staircase. A rotary wheel type SOBP filter may be used as the SOBP device. The SOBP device 21 is mounted on a support member 30, which includes a threaded hole meshing with a ball screw 32 and a through-hole 38. The upper end of the ball screw 32 is attached to the casing 16 in a rotatable manner. The lower end of the ball screw 32 is coupled to an AC servomotor 31, which is mounted on the casing 16. An encoder 33 is coupled to the rotating shaft of the AC servomotor 31. The support member 30 is mounted, in a movable manner, on a linear guide 34, which is installed in the casing 16. The casing 16 includes a bolus retainer 35. A linear actuator is composed by a combination of the AC servomotor 25 and the ball screw 27, by a combination of the AC servomotor 26 and the ball screw 28, and by a combination of the AC servomotor 31 and the ball screw 32.

The configuration of the scattering device 19 will now be described in detail with reference to FIG. 3. The scattering device 19 includes a plurality of scattering device controllers 40, each of which has a compressed-air cylinder 41 and a piston rod 42 that is coupled to a piston (not shown) installed within the compressed-air cylinder 41. The scattering device controllers 40 are mounted on a support frame 39. The scattering device 19 includes scatterers 43A to 43F, which vary in thickness in the direction of ion beam propagation (the direction of a beam axis 14). These scatterers are mounted on the respective scattering device controllers 40 (one scatterer on each scattering device controller). Scatterers 43A to 43F comprise tungsten, which minimizes the loss of ion beam energy in relation to the amount of ion beam scattering. The scatterers may alternatively be made of a material that contains lead or other substance having a high atomic number in addition to tungsten. Compressed-air pipes 49, which each have a solenoid valve 50, are connected to the respective compressed-air cylinders 41 of the scattering device controllers 40. Each compressed-air pipe 49 is connected to a compressed-air supply device (not shown). The support frame 39 is mounted on the top of a support frame 44 of the range adjustment device 20.

As shown in FIG. 4, the range adjustment device 20 includes a plurality of absorber controllers 45, each of which has a compressed-air cylinder 46 and a piston rod 47 that is coupled to a piston (not shown) installed within the compressed-air cylinder 46. These absorber controllers 45 are mounted on the support frame 44. The range adjustment device 20 includes absorbers 48A to 48F, which vary in thickness in the direction of the beam axis 14. These absorbers are mounted on the respective absorber controllers 45 (one absorber on each absorber controller). Each absorber comprises resin that contains hydrocarbon or other substance having a low atomic number. Compressed-air pipes 51, which each have a solenoid valve 52, are connected to the respective compressed-air cylinders 46 of the absorber controllers 45. Each compressed-air pipe 51 is connected to a compressed-air supply device (not shown). The support frame 44 is mounted on the top of the support member 24.

A limit switch is provided for each of the scattering device controllers 40 of the scattering device 19 and the absorber controllers 45 of the range adjustment device 20. The limit switches for the scattering device controllers 40 detect an associated scatterer when it reaches a predefined position for ion beam passage. The limit switches for the absorber controllers 45 detect an associated absorber when it reaches a predefined position. The above scattering device and range adjustment device may alternatively be such that two opposing sphenoid plates are included and continuously repositioned so as to vary the thickness of their overlap.

TABLE 1

| Irradiation field size | Range | Incident energy Eg | Scatterer thickness | Absorber thickness | SC + RS position | Wb11 | Wb12 |
|---|---|---|---|---|---|---|---|
| φ260 [mm] | 40 [mm] . . | 100 [MeV] | 2.05 [mm] . . | 50 [mm] . . | −74 [mm] . . | 171.5 [A] | 203.3 [A] |
| | 90 [mm] 91 [mm] . . | 150 [MeV] | 3.25 [mm] . . | 0 [mm] 59 [mm] . . | −1 [mm] −72 [mm] . . | 252.2 [A] | 301.9 [A] |
| | 150 [mm] 151 [mm] . . | 200 [MeV] | 5.10 [mm] . . | 0 [mm] 6.9 [mm] . . | −2 [mm] −76 [mm] . . | 335.5 [A] | 403.9 [A] |
| | 220 [mm] 221 [mm] . . | 250 [MeV] | 7.20 [mm] . . | 0 [mm] 79 [mm] . . | 0 [mm] −80 [mm] . . | 411.0 [A] | 503.9 [A] |
| | 300 [mm] | | | | | | |
| φ180 [mm] | 40 [mm] . . | 100 [MeV] | 1.50 [mm] . . | 55 [mm] . . | 0 [mm] −80 [mm] . . | 124.1 [A] | 146.8 [A] |
| | 95 [mm] 96 [mm] . . | 150 [MeV] | 2.65 [mm] . . | 0 [mm] 59 [mm] . . | −1 [mm] −79 [mm] . . | 182.5 [A] | 218.8 [A] |
| | 155 [mm] 156 [mm] . . | 200 [MeV] | 3.80 [mm] . . | 0 [mm] 74 [mm] . . | 0 [mm] −85 [mm] . . | 242.5 [A] | 291.5 [A] |
| | 230 [mm] 231 [mm] . . | 250 [MeV] | 5.20 [mm] . . | 0 [mm] 89 [mm] . . | 0 [mm] −89 [mm] . . | 296.0 [A] | 363.9 [A] |
| | 320 [mm] | | | 0 [mm] | 0 [mm] | | |

The particle beam therapy system according to the present embodiment includes a control system 70, which has an irradiation controller 54, drive controllers 56–58, and a scanning magnet controller 36. A memory 55 in the irradiation controller 54 stores irradiation condition information, which is shown in Table 1. The items of the irradiation condition information are the length of a diseased part 62 in a direction perpendicular to the beam axis 14 (irradiation field size), the location of the diseased part 62 in the direction of the depth (range), the energy incident on the irradiation apparatus 15 (incident Eg), the thickness of the scatterer (scatterer thickness), the thickness of the absorber (absorber thickness), the position of the scattering device 19/range adjustment device 20 (SC+RS position), the exciting current of the first scanning magnet 17 (Wb11), and the exciting current of the second scanning magnet 18 (Wb12). The relationship between the information about the irradiation field size, range, and incident energy, which is the therapy plan information, and the scatterer thickness, absorber thickness, SC+RS position, Wb11, and Wb12 is to be predefined in accordance with the results of calculations and experiments. The SC+RS position is a position based on a starting point that is the first reference position for the scattering device 19 and range adjustment device 20. A therapy plan device 53 stores the therapy plan information (irradiation field size, ion beam incidence direction, range for incidence direction, incident energy, etc.) about a patient 61 who is to be treated. The memory 55 stores the position of each SOBP device 21 (SOBP position) as the irradiation condition information in relation to the spread-out Bragg peak width (SOBP width) shown in Table 2 and the incident energy for the interior of a patient's body, which is one item of therapy plan information. The position of each SOBP device 21 is a position based on a starting point that is the second reference position for the SOBP device 21. An alternative configuration in which the irradiation controller 54, drive controllers 56–58, and scanning magnet controller 36 are not furnished may be employed so that the control system 70 exercises the respective functions of the irradiation controller 54, drive controllers 56–58, and scanning magnet controller 36.

information about a scatterer and absorber as well as a drive instruction signal to the drive controller 56. In accordance with the scatterer thickness information, the drive controller 56 selects one or more scatterers from the scatterers in the scattering device 19. If, for instance, the total thickness of the scatterers 43B and 43C agrees with the scatterer thickness information, the drive controller 56 selects the scatterers 43B and 43C. The drive controller 56 opens the solenoid valves 50 on the compressed-air pipes 49 connected to the scattering device controllers 40 that respectively operate scatterers 43B and 43C. Compressed air is then supplied to the cylinders 41 of the associated scattering device controllers 40 so that the piston rods 42 move to push the scatterers 43B and 43C to the above-mentioned selected position. The remaining scatterers are positioned at a location away from the position of ion beam passage. Further, the drive controller 56 selects one or more absorbers from the absorbers in the range adjustment device 20 in such a manner that the resulting total absorber thickness agrees with the informa-

TABLE 2

| | Incident energy | | | | | | | |
|---|---|---|---|---|---|---|---|---|
| | 100 [MeV] | | 150 [MeV] | | 200 [MeV] | | 250 [MeV] | |
| SOBP width | SOBP No. | SOBP position | SOBP No. | SOBP position | SOBP No. | SOBP position | SOBP No. | SOBP position |
| 10 [mm] | E100S010 | 0 [mm] | E150S010 | 0 [mm] | E200S010 | 0 [mm] | E250S010 | 0 [mm] |
| 20 [mm] | E100S020 | −100 [mm] | E150S020 | −80 [mm] | E200S020 | −80 [mm] | E250S020 | −80 [mm] |
| 30 [mm] | E100S030 | −150 [mm] | E150S030 | −140 [mm] | E200S030 | −130 [mm] | E250S030 | −130 [mm] |
| 40 [mm] | E100S040 | −200 [mm] | E150S040 | −180 [mm] | E200S040 | −170 [mm] | E250S040 | −170 [mm] |
| 50 [mm] | E100S050 | −230 [mm] | E150S050 | −220 [mm] | E200S050 | −210 [mm] | E250S050 | −210 [mm] |
| 60 [mm] | E100S060 | −260 [mm] | E150S060 | −240 [mm] | E200S060 | −230 [mm] | E250S060 | −230 [mm] |
| 70 [mm] | — | — | E150S070 | −260 [mm] | E200S070 | −240 [mm] | E250S070 | −240 [mm] |
| 80 [mm] | — | — | E150S080 | −270 [mm] | E200S080 | −250 [mm] | E250S080 | −250 [mm] |
| 90 [mm] | — | — | — | — | E200S090 | −250 [mm] | E250S090 | −250 [mm] |
| 100 [mm] | — | — | — | — | E200S100 | −260 [mm] | E250S100 | −260 [mm] |
| 110 [mm] | — | — | — | — | | | E250S110 | −260 [mm] |
| 120 [mm] | — | — | — | — | | | E250S120 | −260 [mm] |

A plurality of SOBP devices 21 are prepared as denoted by E150S010, E150S020, etc. in Table 2. E150S010, E150S020, and other similar entries in the table are the numbers of the SOBP devices (SOBP No.). These SOBP devices 21 differ, for instance, in sphenoid member height and staircase section width and height. The SOBP devices 21 are selectively mounted beforehand on the support member 30 in accordance with the energy incident on the irradiation apparatus 15 and the SOBP width. The SOBP width is determined according to the length of a diseased part in the direction of ion beam propagation.

Prior to positioning a patient 61 in relation to the irradiation apparatus 15, the irradiation controller 54 receives the therapy plan information (irradiation field size (irradiation field information), range (range information), incident energy (beam energy information), etc.) about the patient 61 from the therapy plan device 53 and stores it in the memory 55. The irradiation controller 54 selects a scatterer thickness and absorber thickness as needed from the irradiation condition information in accordance with the therapy plan information. The greater the ion beam incident energy, the greater the selected scatterer thickness. The shorter the requested range, the greater the selected absorber thickness. Further, the irradiation controller 54 selects an "SC+RS position" in accordance with the selected thickness information (range information) about a scatterer and absorber. The irradiation controller 54 outputs the selected thickness tion about the selected absorber thickness. If, for instance, the thickness of the absorber 48E agrees with the absorber thickness information, the drive controller 56 selects the absorber 48E. The drive controller 56 opens the solenoid valve 52 on the compressed-air pipe 51 connected to the absorber controller 45 that operates the absorber 48E. Compressed air is then supplied to the cylinder 41 of the associated absorber controller 45 so that the piston rod 47 moves to push the absorber 48E to the above-mentioned selected position. The remaining absorbers are positioned at a location away from the position of ion beam passage. When the associated scatterers and absorber reach the selected positions, the associated limit switches actuate to generate position signals and convey them to drive the controller 56. The drive controller then outputs scatterer/absorber relocation completion information to the irradiation controller 54.

The irradiation controller 54 outputs the "SC+RS position" information, that is, the first position information, as well as a drive instruction signal to the drive controller 57. In accordance with the first position information, the drive controller 57 rotates the AC servomotors 25 and 26 in order to move the support member 24 to a specified position. Consequently, the scattering device 19 and range adjustment device 20 move to positions that correspond to the first position information. The detection signal of the encoder 29 notifies the drive controller 57 that the support member 24 has reached the specified position. The irradiation controller 54 does not output a drive instruction signal to drive the controller 58 because the required SOBP width is 10 mm. For treatment of a patient 61 who requires an SOBP width of 30 mm, the irradiation controller 54 outputs the positional information about the SOBP devices 21, that is, the second position information, as well as a drive instruction signal to the drive controller 58. In accordance with the second position information, the drive controller 58 rotates the AC servomotor 31 in order to move the support member 30 to a specified position. The SOBP devices 21 move to positions that correspond to the second position information. The detection signal of the encoder 33 notifies the drive controller 57 that the support member 30 has reached the specified position.

Figure 13A:
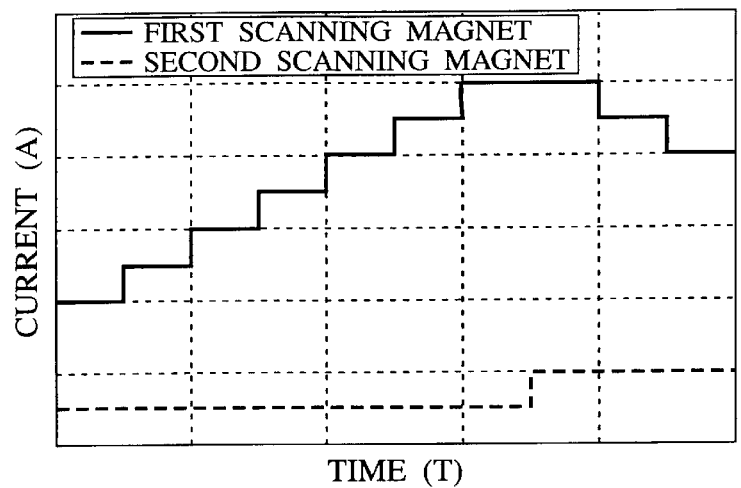
FIG. 13A is a graph that relates to scanning in a seventh embodiment and illustrates the exciting current patterns for scanning magnets of an irradiation apparatus.
Figure 13B:
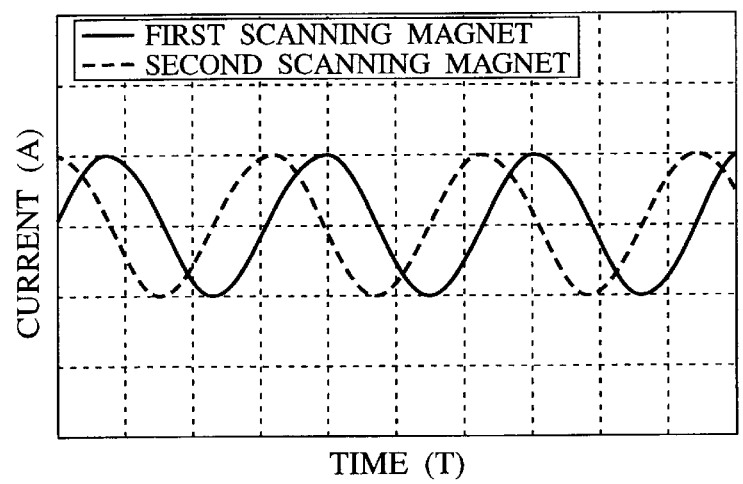
FIG. 13B is a graph that relates to the first embodiment and illustrates the exciting current patterns for scanning magnets of an irradiation apparatus.

The irradiation controller 54 acquires the information about the irradiation field size and incident energy for the patient 61 from the memory 55 and uses the acquired information to select the respective exciting currents for the first scanning magnet 17 and second scanning magnet 18 from the aforementioned irradiation condition information. The selected information about the respective exciting currents (e.g., the information about the respective exciting currents for the scanning magnets shown in FIG. 13B) is conveyed to the scanning magnet controller 36. In accordance with the information about the respective exciting currents, the scanning magnet controller 36 controls the respective exciting currents to be supplied to the first scanning magnet 17 and second scanning magnet 18 for the purpose of rotating the ion beam in such a manner as to draw a circle in a plane perpendicular to the beam axis 14. The resulting circle is called a wobbling circle. More specifically, the first scanning magnet 17 conducts a scan to move the ion beam in the X-direction within the above circle, and then the second scanning magnet 18 conducts a scan to move the ion beam in the direction of the Y-axis, which is perpendicular to the X-axis, within the above circle. Thanks to such a coordinated ion beam scanning operation performed by the first scanning magnet 17 and second scanning magnet 18, the ion beam moves in a circular manner in the above plane. This ion beam scan is conducted when the irradiation apparatus 15 emits an ion beam. The size of the wobbling circle is determined in accordance with the dimension of a diseased part 62 in a direction perpendicular to the direction of ion beam propagation.

Ion beam adjustments and other pretreatment preparations are made after the selected scatterers and absorber are set at the ion beam passage positions with the scattering device 19, range adjustment device 20, and SOBP devices 21 moved to the specified positions. Further, a bolus 22 for the patient 61 is set in the bolus retainer 35 with a collimator 23 set in a casing 16 below the bolus retainer 35. After these preparations are completely made, the patient couch 59 is moved until the diseased part 62 of the patient 61 aligns with the beam axis 14 of the irradiation apparatus 15. Upon completion of alignment, a treatment starts. The operator enters a treatment start signal via an operating console (not shown). Upon receipt of the treatment start signal, an accelerator controller (not shown) operates so that the synchrotron 4 emits an ion beam. As described earlier, the ion beam reaches the irradiation apparatus 15. In accordance with the above-mentioned entered treatment start signal, the irradiation controller 54 outputs an ion beam scan start signal and the aforementioned information about exciting currents to the scanning magnet controller 36. The scanning magnet controller 36 controls the exciting currents to scan the ion beam as described above.

The scanned ion beam passes through the scatterers 43B and 43C. Being scattered by the scatterers, the ion beam spreads in a conical pattern in relation to the direction of ion beam propagation. The ion beam then passes through the absorber 48E. The absorber reduces the ion beam energy to adjust the in vivo range of the ion beam. Further, the ion beam passes through the SOBP devices 21. The sphenoid members of the SOBP devices 21 vary in thickness in the direction of ion beam propagation. Due to the portions that vary in thickness, the degree of energy attenuation in the ion beam, which is spread by the scatterers and scanned by the scanning magnets, varies with the SOBP device portion through which the ion beam passes. After passage through the SOBP devices 21, the resulting ion beams, which now differ from each other in energy, respectively form Bragg peaks at various in vivo locations. This results in an increased uniformity of radiation dose distribution in the direction of the beam axis 14.

After passage through the SOBP devices 21, the ion beams pass through the bolus 22. The bolus adjusts the ranges of the ion beams in accordance with the shape of the diseased part 62 in the direction of ion beam propagation. The collimator 23 eliminates ion beams that are positioned, after passage through the bolus 22, outside the projection of the diseased part 62 in the direction of the beam axis 14. In other words, the collimator 23 allows ion beams positioned inside the projection to pass therethrough. The diseased part 62 is exposed to ion beams that pass through the collimator 23.

Figure 5:
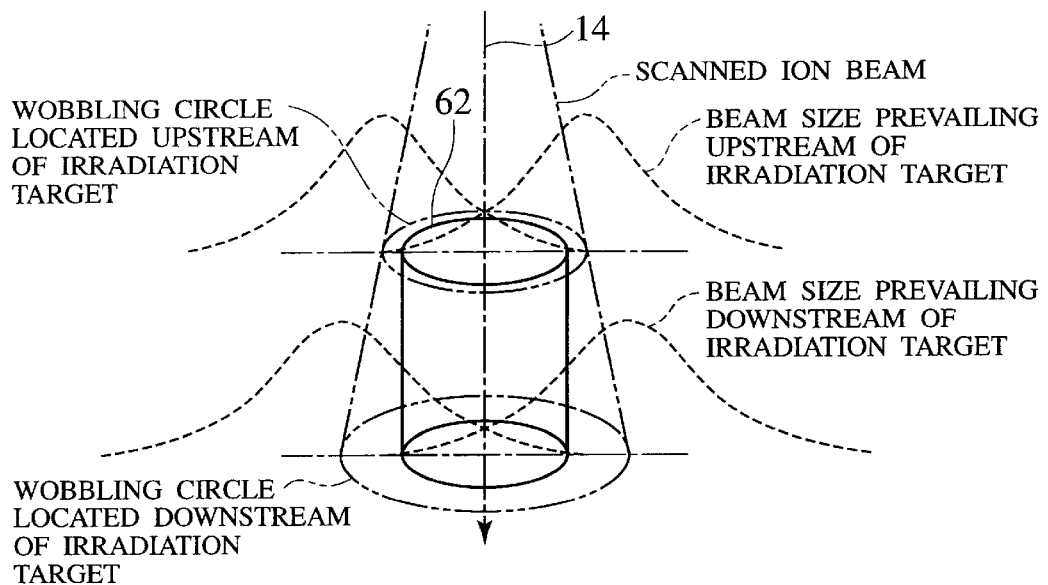
FIG. 5 illustrates an ion beam that is scanned by a scanning magnet when an irradiation apparatus shown in FIG. 2, that is, an SOBP device, is located downstream of the scanning magnet.

In the present embodiment, the size of the wobbling circle located downstream of the diseased part 62 in the direction of ion beam propagation (irradiation target downstream wobbling circle) and the size of the wobbling circle located upstream of the diseased part 62 in the direction of ion beam propagation (irradiation target upstream wobbling circle) are defined simply according to the distance from the scanning focus positions of the same scanning magnets 17, 18 (FIG. 5). Meanwhile, the ion beam size and quantity on the downstream side are the size and quantity of an ion beam passing through thin portions of the SOBP devices 21. The ion beam size and quantity on the upstream side are the total ion beam size and quantity of ion beams passing through thin and thick portions of the SOBP device 21. When the scatterers, absorber, and SOBP devices 21 are moved and set to their respective positions so as to optimize the ratio between the upstream wobbling circle and ion beam size and the ratio between the downstream wobbling circle and ion beam size, the uniformity of radiation dose distribution for the diseased part can be enhanced while keeping the radiation dose rate high. The irradiation target is determined according to the shape of the diseased part 62. It may occasionally be rendered larger than the diseased part so as to leave a certain margin.

In the present embodiment, the scatterers (e.g., scatterers 43B and 43C) at an ion beam passage position are moved in the direction of ion beam propagation. Therefore, the ion beam scatter size prevailing at the position of the diseased part 62 (the enlarged ion beam size in a direction perpendicular to the direction of ion beam propagation) can be varied. More specifically, the scatter size decreases when the scatterers are moved toward the diseased part 62 and increases when the scatterers are moved away from the diseased part 62. When the scatterers move in the direction of ion beam propagation, the ion beam scatter size can be optimized so as to provide uniform radiation dose distribution in the direction of ion beam propagation without changing the in vivo ion beam range. Consequently, the distribution of radiation dose administered to the diseased part 62 can be adjusted. More specifically, the scatterers are moved away from the diseased part 62 when the ion beam scatter size is smaller than the optimum scatter size, and moved toward the diseased part 62 when the ion beam scatter size is larger than the optimum scatter size.

When the thickness of the absorber in the ion beam passage region increases, the ion beam scatter size becomes larger than the optimum scatter size and the radiation dose distribution for the diseased part 62 becomes worse. In the present embodiment, however, the selected absorber is moved in the direction of ion beam propagation. Therefore, it is possible to inhibit the radiation dose distribution for the diseased part 62 from deteriorating due to an ion beam scatter size change, which arises from an ion beam range adjustment that is made with an absorber selected. As a result, the radiation dose distribution for the optimum scatter size can be obtained. The move of the absorber adjusts absorber-induced changes in the radiation dose distribution for the diseased part 62 without changing the ion beam range. When the thickness of the selected absorber increases, the absorber is moved further downstream in the direction of ion beam propagation.

A plurality of SOBP devices 21, which vary in the SOBP width, are furnished. As described earlier, one SOBP device 21 is selected and set. The SOBP devices 21 provide different ion beam scatter sizes depending on the attainable SOBP width. As the scatter size of an SOBP device 21 increases, the resulting position is shifted downstream. Thanks to this shift, the ion beam scatter size is optimized. This uniforms the radiation dose distribution for the diseased part 62 in a direction perpendicular to the direction of ion beam propagation.

As described above, the present embodiment can uniform the radiation dose distribution for the diseased part 62 because it can move the scattering device 19, range adjustment device 20, and SOBP device 21 in the direction of ion beam propagation. Further, the present embodiment increases the radiation dose rate because the ion beam usability improves.

In the present embodiment, the scattering device 19 is installed in the range adjustment device 20. Therefore, these devices can be moved together by the same AC servomotors 25, 26, which serve as drive devices. Consequently, the configuration of the present embodiment is simpler than in cases where the scattering device 19 and range adjustment device 20 are moved separately by respective drive devices. In the present embodiment, the scattering device 19 and range adjustment device 20 are integral with each other with absorbers positioned close to scatterers. Therefore, the size of an ion beam incident on an absorber is rendered small so that the length and width of each absorber in a plane perpendicular to the beam axis 14 can be reduced. This makes the range adjustment device 20 smaller. Although the influence of absorber-induced scattering is exercised depending on the amount of absorber insertion, the present embodiment moves absorbers and scatterers together in the direction of ion beam propagation. Therefore, it is possible to decrease the amount of absorber travel in the direction of such propagation and increase the distance between the diseased part 62 and absorbers. Since the distance is increased with scatterers and absorbers positioned close to each other, the radiation dose distribution penumbra (half shadow) beyond the diseased part 62 decreases. In the present embodiment, the absorbers and scatterers are equal in the amount of travel along the beam axis 14. Since the scattering device 19 and range adjustment device 20, which are integral with each other, move along the beam axis 14, the degree of variation in the radiation dose distribution for the diseased part 62 can be decreased without regard to the ion beam range determined according to an absorber selection. Due to the use of the scattering device 19 and range adjustment device 20 that are integral with each other, the present embodiment positions a selected absorber near scatterers to reduce the size of an ion beam incident on the absorber. As a result, each absorber can be reduced in size so as to downsize the irradiation apparatus 15.

The present embodiment uses the functions of the control system 70, particularly the functions of the irradiation controller 54 and drive controller 56, to easily move the scatterer of a first scattering device 19 in the direction of ion beam propagation and set it at a preselected position. In particular, the irradiation controller 54 can place the scatterer of the first scattering device 19 in the above preselected position using the therapy plan information about the patient 61, more specifically, the range (range information).

Figure 6A:
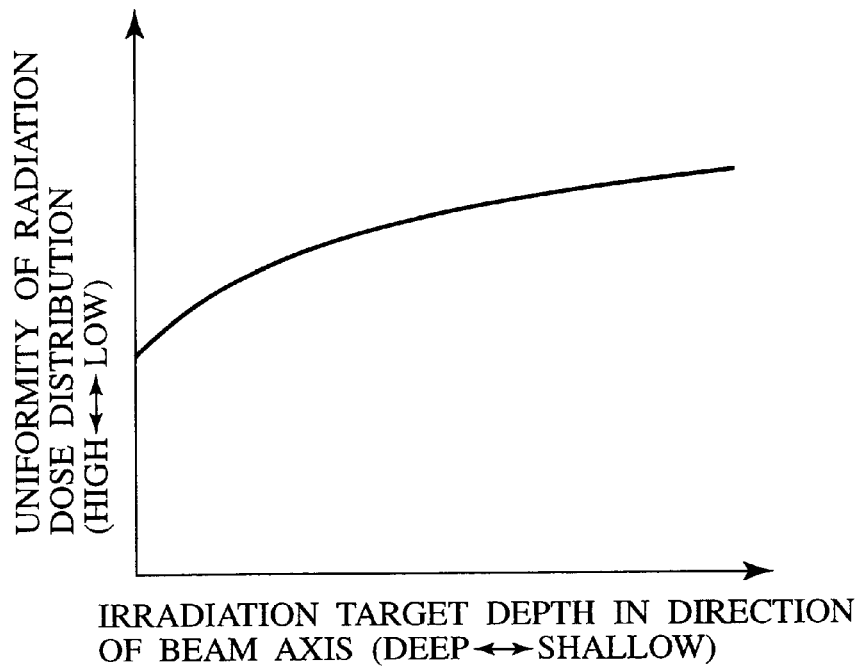
FIG. 6A shows a characteristics graph that prevails during the use of a conventional irradiation apparatus and illustrates the relationship between the irradiation target depth in the direction of the beam axis and the uniformity of radiation dose distribution.
Figure 6B:
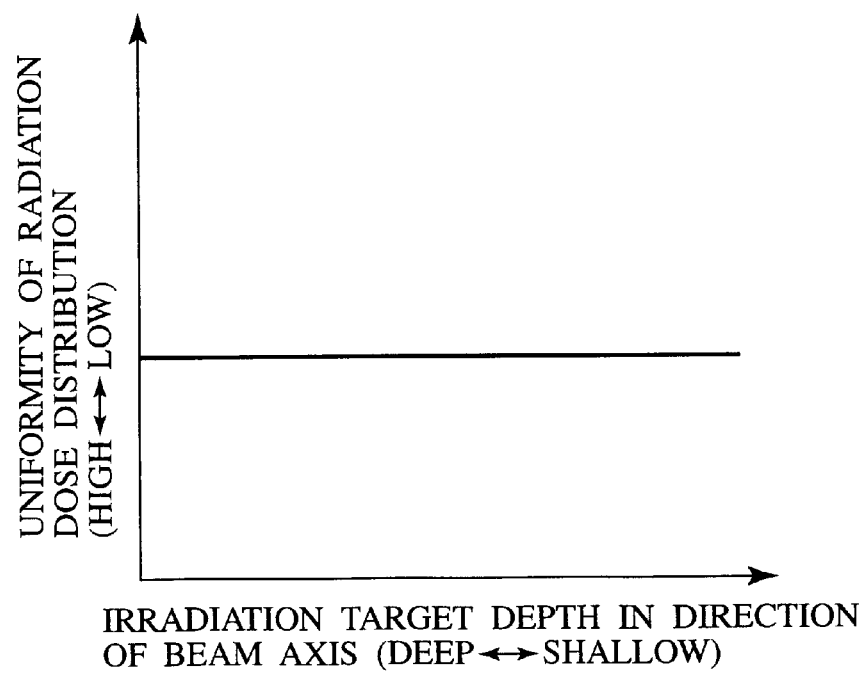
FIG. 6B shows a characteristics graph that prevails during the use of an irradiation apparatus shown in FIG. 2 and illustrates the relationship between the irradiation target depth in the direction of the beam axis and the uniformity of radiation dose distribution.

In the present embodiment, the radiation dose distribution for the irradiation target based on ion beam irradiation is uniform in the direction of the in vivo depth as shown in FIG. 6B. The radiation dose distribution shown in FIG. 6B is obtained when the range adjustment device 20 is moved in accordance with the present embodiment. In a conventional configuration in which the scattering device 19, range adjustment device 20, and SOBP device 21 are not moved, the radiation dose distribution within the irradiation target varies in the direction of the in vivo depth as shown in FIG. 6A. Such a variation in the radiation dose distribution can be significantly inhibited by the present embodiment. The examples shown in FIGS. 6A and 6B relate to a case where ion beams having the same energy are used for irradiation.

Figure 7A:
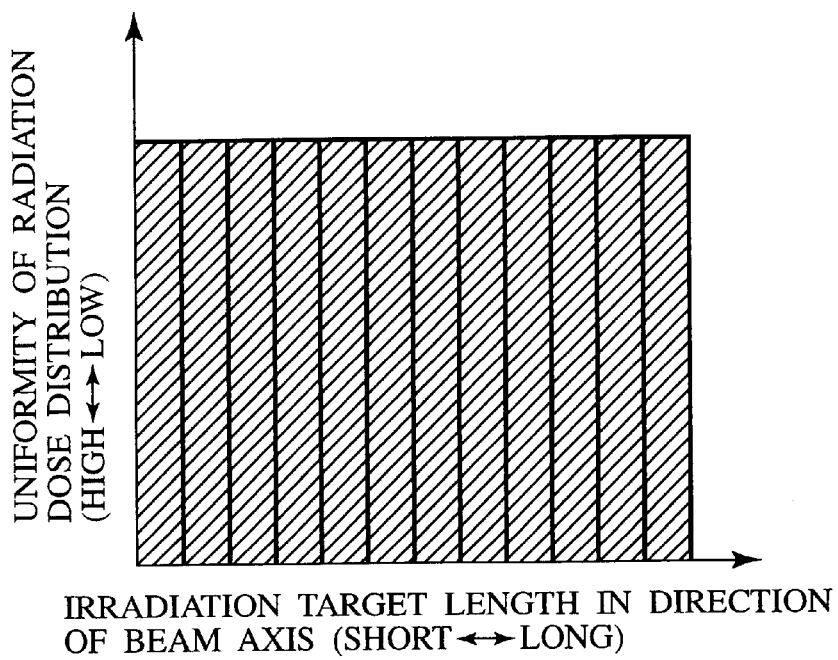
FIG. 7A shows a characteristics graph that prevails during the use of a conventional irradiation apparatus and illustrates the relationship between the irradiation target length in the direction of the beam axis and the uniformity of radiation dose distribution.
Figure 7B:
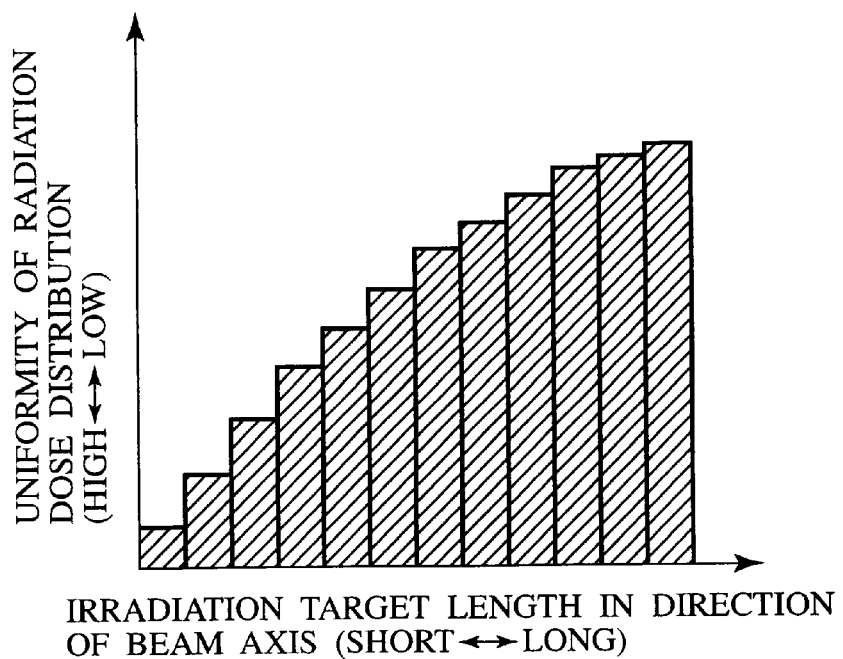
FIG. 7B shows a characteristics graph that prevails during the use of an irradiation apparatus shown in FIG. 2 and illustrates the relationship between the irradiation target length in the direction of the beam axis and the uniformity of radiation dose distribution.

FIG. 7A shows the uniformity of radiation dose distribution for an irradiation target in a conventional configuration. In the conventional configuration, the radiation dose distribution remains uniform no matter whether the irradiation target length in the direction of the depth varies. As shown in FIG. 7B, the present embodiment provides a higher degree of radiation dose distribution uniformity when the irradiation target length in the direction of the depth decreases. The characteristics shown in FIG. 7B are obtained when the SOBP device 21 is moved in accordance with the present embodiment.

Although the present embodiment moves the scattering device 19 and range adjustment device 20, which are integral with each other, and the SOBP device 21 along the beam axis 14, an alternative configuration may be employed so as to move either a combination of the scattering device 19 and range adjustment device 20 or the SOBP device 21. When the employed configuration renders the SOBP device 21 movable and the scattering device 19 and range adjustment device 20 immovable, the radiation dose distribution variation, which occurs in the diseased part 62 in response to the selected absorber, is not adjustable; however, the degree of uniformity of radiation dose distribution for the diseased part 62 is higher than in the conventional configuration.

In the present embodiment, the scattering device 19 and range adjustment device 20, which are integral with each other, may alternatively be positioned upstream of the first scanning magnet 17. Since the scattering device 19 is located upstream of the first scanning magnet 17 in this alternative configuration, the degree of ion beam scattering by the scattering device 19 can be reduced. Consequently, the scatterer thickness of the scattering device 19 can be decreased so as to render the scattering device 19 compact.

Since the present embodiment positions the range adjustment device 20 upstream of the first scanning magnet 17, the effective radiation source distance can be rendered longer than when the range adjustment device 20 is positioned downstream of the first scanning magnet 17, and the effective radiation source size can be further reduced. As a result, the half shadow further decreases in size. Further, when the range adjustment device 20 is positioned upstream of the first scanning magnet 17, the absorber size (absorber thickness) increases, thereby reducing the ion beam energy and acquiring a larger wobbling circle. This increases the degree of freedom in selecting a ratio between the ion beam scatter size for the diseased part 62 and the size of the wobbling circle.

Although the present embodiment is provided with the range adjustment device 20, an alternative configuration, which is without the range adjustment device 20, may be employed so that the synchrotron 4 adjusts the energy given to the ion beam at the time of acceleration for the purpose of adjusting the ion beam range within the body of the patient 61. Another alternative configuration may also be formed so as to obtain a desired ion beam range by preselecting a desired bottom thickness of the bolus 22.

Second Embodiment

Figure 8:
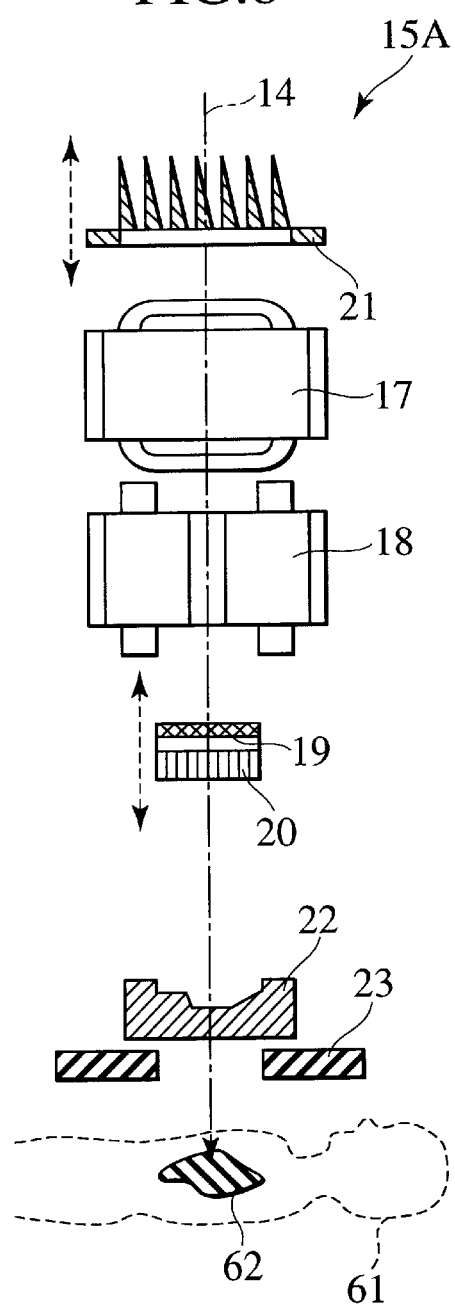
FIG. 8 illustrates the configuration of an irradiation apparatus for use with a particle beam therapy system in accordance with a second embodiment of the present invention.

A particle beam therapy system according to a second embodiment of the present invention will now be described. The particle beam therapy system according to the present embodiment is configured so that the irradiation apparatus 15 in the particle beam therapy system 1 shown in FIG. 1 is replaced by an irradiation apparatus 15A shown in FIG. 8. The irradiation apparatus 15A differs from the irradiation apparatus 15 in positions of the SOBP device 21 and the components associated with it. As shown in FIG. 8, the irradiation apparatus 15A is configured so that the SOBP device 21 is positioned upstream of the first scanning magnet 17. The support member 30, AC servomotor 31, ball screw 32, encoder 33, and linear guide 34 are also positioned upstream of the first scanning magnet 17 and mounted within the casing 16. A rotary wheel type SOBP filter may be used as the SOBP device.

Figure 9:
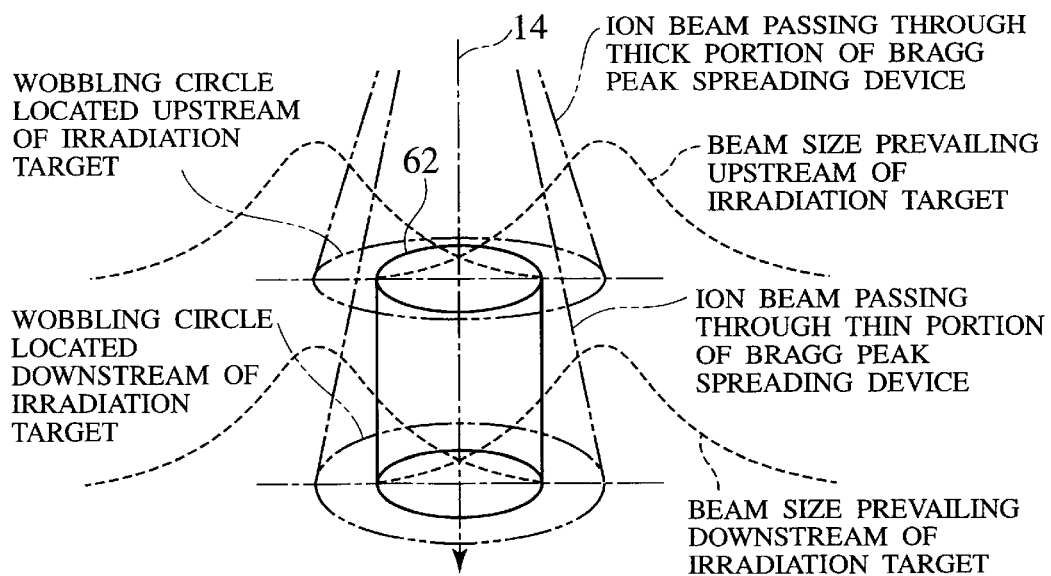
FIG. 9 illustrates an ion beam that is scanned by a scanning magnet when an irradiation apparatus shown in FIG. 8, that is, an SOBP device, is located upstream of the scanning magnet.
Figure 10A:
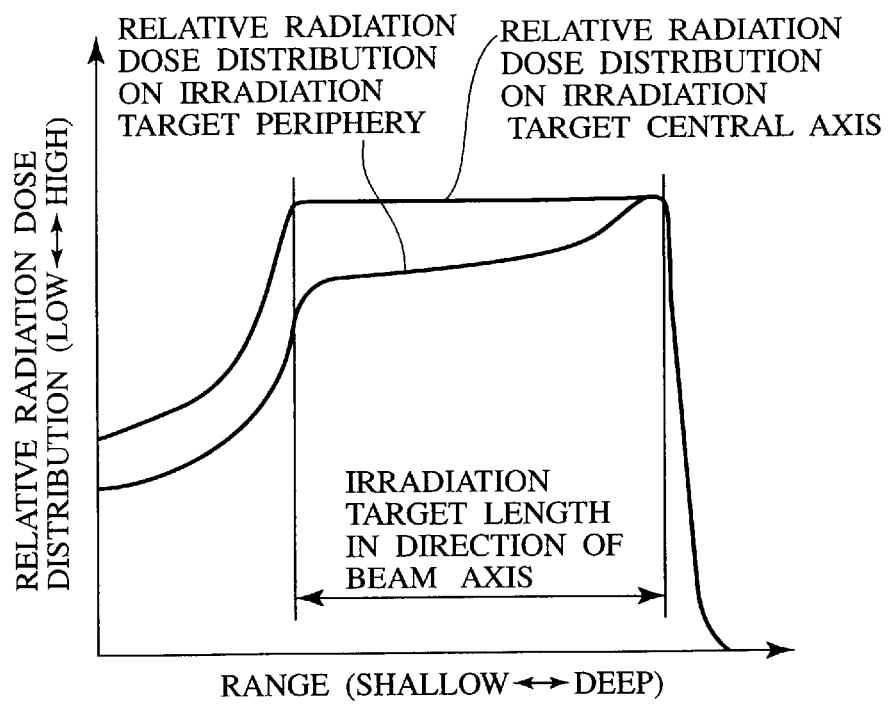
FIG. 10A shows a characteristics graph that prevails during the use of a conventional irradiation apparatus and illustrates the relationship between the ion beam range on the irradiation target central axis and periphery and the relative radiation dose distribution.
Figure 10B:
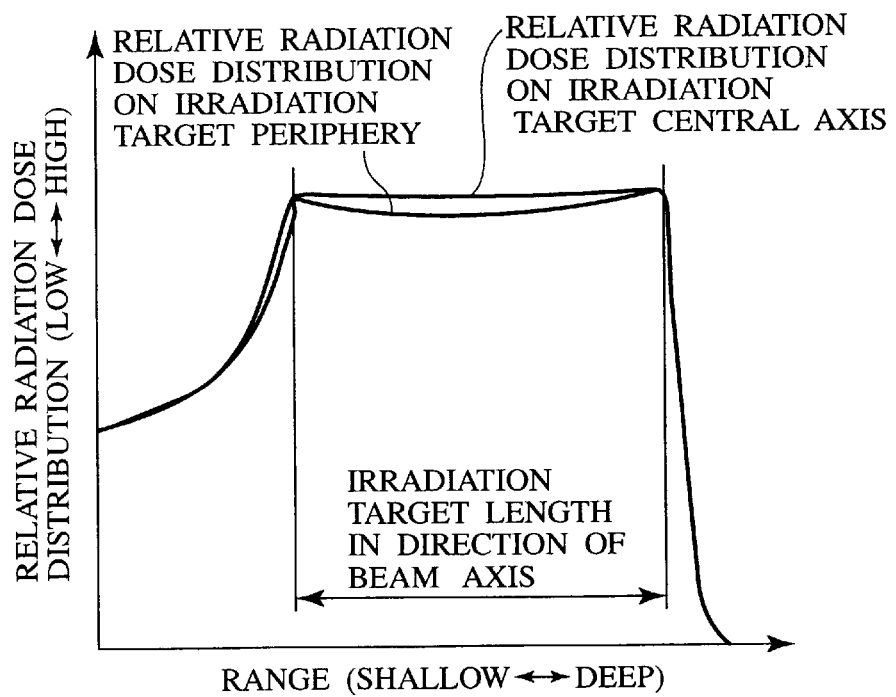
FIG. 10B shows a characteristics graph that prevails during the use of an irradiation apparatus shown in FIG. 2 and illustrates the relationship between the ion beam range on the irradiation target central axis and periphery and the relative radiation dose distribution.

The ion beam passing through a thin portion of the SOBP device 21 is high in energy. Therefore, the amount of scanning provided by the first and second scanning magnets is small. However, the ion beam passing through a thick portion of the SOBP device 21 is low in energy. Therefore, the amount of scanning provided by the first and second scanning magnets is larger than the amount of scanning provided for the ion beam passing through the thin portion. As a result, the spread angle of the ion beam passing through the thick portion after scanning by the first and second scanning magnets is greater than the spread angle of the ion beam passing through the thin portion after scanning as shown in FIG. 9. The wobbling circle located upstream of the irradiation target is formed by the ion beam passing through the thick portion, whereas the wobbling circle located downstream of the irradiation target is formed by the ion beam passing through the thick portion. Therefore, the SOBP device 21 is moved and positioned so as to optimize the ratio between the circle that is drawn in an in vivo, shallow range region by an ion beam scanned by the first and second scanning magnets and composed by various energy components, and the ion beam size provided by ion beams of various energy components, and the ratio between the circle drawn in a deep range region by an ion beam and the ion beam size provided by ion beams of various energy components. Consequently, as shown in FIG. 10B, the relative radiation dose distribution on the irradiation target beam axis 14 (central axis) becomes uniform in the direction of the in vivo depth and the uniformity of relative radiation dose distribution on the irradiation target periphery increases in the direction of the depth. Further, the relative radiation dose distribution on the irradiation target periphery according to the present embodiment shown in FIG. 10B exhibits a higher degree of uniformity than the relative radiation dose distribution on the periphery according to the first embodiment (FIG. 10A) in which the SOBP device 21 is positioned downstream of the second scanning magnet 18. In other words, the first embodiment increases the degree of uniformity of radiation dose distribution by balancing the radiation dose distributions, in a direction perpendicular to the beam axis 14, for the deep and shallow irradiation target positions. Unlike the first embodiment, the present embodiment eliminates the difference between the radiation dose distributions for the deep and shallow positions.

The present embodiment provides the advantages that are provided by the first embodiment. In addition, the present embodiment makes it possible to reduce the sizes of ion beams and the SOBP device 21 because the SOBP device 21 is positioned upstream of the first scanning magnet 17.

An alternative configuration may be employed for the present embodiment so that either a combination of the scattering device 19 and range adjustment device 20 or the SOBP device 21 is movable.

In another alternative configuration for the present embodiment, a combination of the scattering device 19 and range adjustment device 20, which are integral with each other, and the drive devices for moving the combination along the beam axis 14 may be both positioned upstream of the SOBP device 21. This alternative configuration makes it possible to render the range adjustment device 20 compact as mentioned earlier.

Third Embodiment

Figure 11:
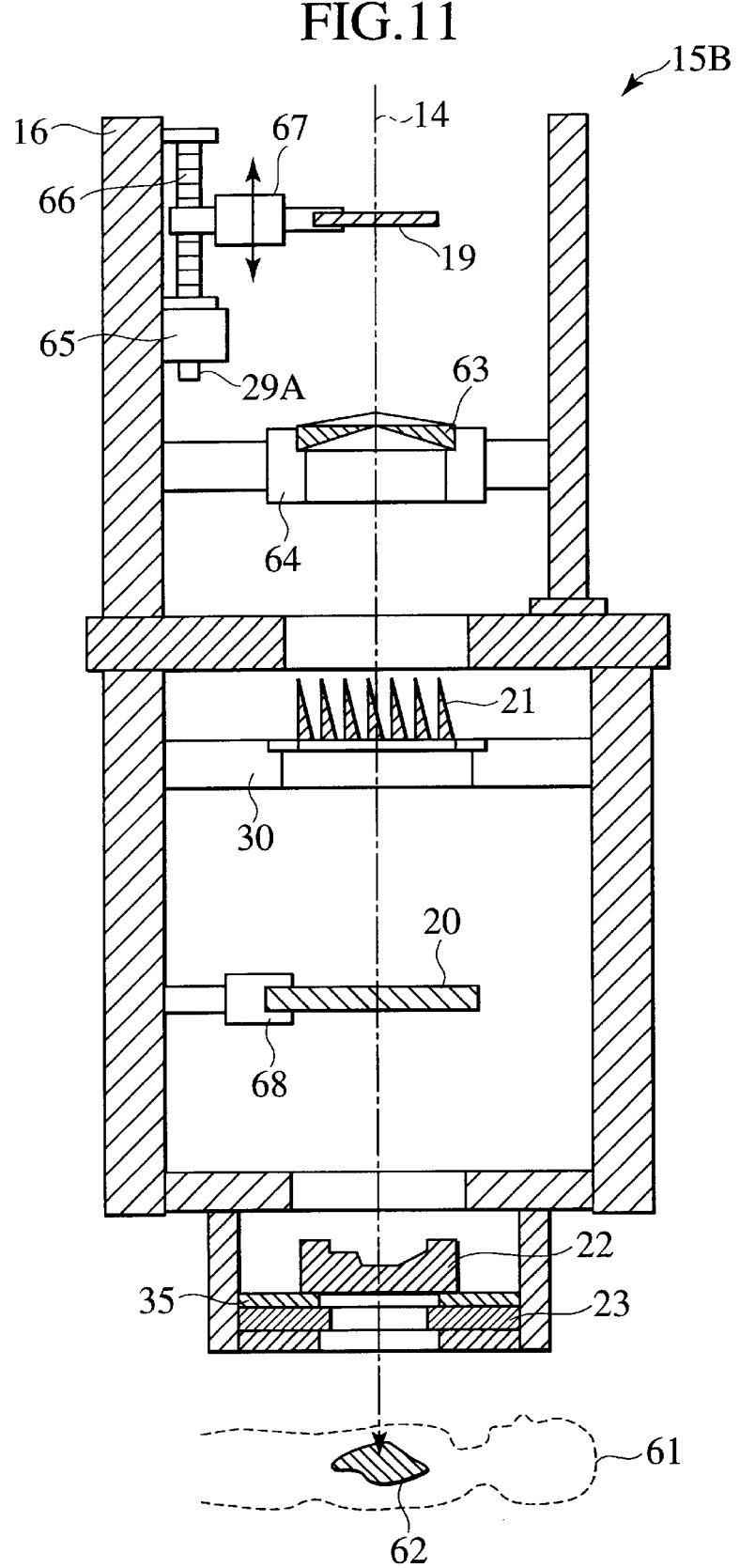
FIG. 11 illustrates the configuration of an irradiation apparatus for use with a particle beam therapy system in accordance with a third embodiment of the present invention.

The foregoing embodiments relate to a particle beam therapy system that is based on a wobbling type irradiation apparatus. A third embodiment of the present invention, that is, a particle beam therapy system based on a scatterer type irradiation apparatus, will now be described. The particle beam therapy system according to the third embodiment is such that the irradiation apparatus 15 in the particle beam therapy system 1 shown in FIG. 1 is replaced by irradiation apparatus 15B, which is a scatterer type, first irradiation apparatus shown in FIG. 11. The particle beam therapy system according to the present embodiment does not include a drive controller 58. The irradiation apparatus 15B includes a scattering device 19 (first scatterer), a scattering device 63 (second scatterer), a SOBP device 21, and a range adjustment device 20, which are mounted within a casing 16 and sequentially arranged from upstream to downstream of ion beam propagation. The casing 16 includes a bolus retainer, which is located downstream of the range adjustment device 20.

The scattering device 19 is mounted on a support member 67. The support member 67 meshes with a ball screw 66, which travels through a threaded hole. The upper end of the ball screw 66 is attached to the casing 16 in a rotatable manner. The lower end of the ball screw 66 is coupled to an AC servomotor 65, which is mounted on the casing 16. An encoder 29A is coupled to the rotating shaft of the AC servomotor 65. The scattering device 63 is mounted on the casing 16 via a support member 64. The SOBP device 21 is mounted on the casing 16 via a support member. The range adjustment device 20 is mounted on the casing 16 via a support member 68. In the present embodiment, the scattering device 63, SOBP device 21, and range adjustment device 20 cannot move along the beam axis 14.

The scattering device 63 is configured so that the degree of ion beam scattering varies from one ion beam incidence point to another. The scattering device 63 includes, for instance, a double-ring scatterer, which comprises a plurality of materials that differ in the degree of scattering. The scattering device 63 is a device for adjusting the ion beam radiation dose distribution. More specifically, the inner and outer structures of scattering device 63 differ from each other. Since the scattering intensity differs between the inner and outer structures, the scattering device 63 makes adjustments to uniform the radiation dose distribution for an overlap between inner- and outer-passing ion beams. Another example of the scatterer for the scattering device 63 would be, for instance, a contoured radiation structure in which the material proportion varies stepwise.

As is the case with the first embodiment, the irradiation controller 54 selects a scatterer thickness and absorber thickness from the irradiation condition information stored in the memory 55 in accordance with patient therapy plan information stored in the memory 55. The memory 55 stores SC position information instead of the "SC+RS position" information, which is shown as part of the irradiation condition information shown in Table 1. The stored SC position information is the positional information about the scattering device 19. The SC position is a position that is based on the first reference position for the scattering device 19. In accordance with the information about selected scatterer thickness, the drive controller 56 selects a scatterer required within the scattering device 19 and exercises control so as to move the selected scatterer to an ion beam passage position. The drive controller 56 also selects an absorber required within the range adjustment device 20 in accordance with the information about selected absorber thickness, and exercises control so as to move the selected absorber to an ion beam passage position. The bolus 22 is set in the bolus retainer 35. Further, the collimator 23 is set at the lower end of the casing 16.

The irradiation controller 54 outputs the SC position information, which is the first position information, as well as a drive instruction to the drive controller 57. In accordance with the SC position information, the drive controller 57 rotates the AC servomotor 65 in order to move the support member 67 to a specified position along the beam axis 14. The drive controller 57 provides drive control over the AC servomotor 65 for the purpose of moving the scattering device 19 in the direction of the beam axis 14 in accordance with the size of the diseased part 62 in a direction perpendicular to the beam axis 14.

After an ion beam is emitted from a rotary irradiation device 10 and incident on irradiation apparatus 15C, it is scattered by the selected scatterer of the scattering device 19, spread in a conical pattern in the direction of ion beam propagation, and entered into the scattering device 63. The ion beam is then scattered by the double-ring scatterer of the scattering device 63 in order to adjust the radiation dose distribution in a plane perpendicular to the beam axis 14. The ion beam then sequentially passes through the Bragg peak spreading device 21, range adjustment device 20, bolus 22, and collimator 23 and falls on the diseased part 62. The Bragg peak spreading device 21 and range adjustment device 20 function the same as described in conjunction with the first embodiment.

Since the present embodiment moves the scatterer in the direction of ion beam propagation, it provides a higher degree of uniformity of radiation dose distribution for the diseased part 62 than a conventional configuration. The present embodiment also improves the ion beam usability and increases the radiation dose rate. When the scattering device 63 moves along the beam axis 14, two problems arise. The first problem is that a high degree of accuracy is required for linearity of movement in the direction of the beam axis 14 because the radiation dose distribution is greatly affected by the concentricity between the scattering device 63 and the beam axis 14. The second problem is that the AC servomotor for drive is required to have an increased capacity because the scattering device 63 is larger and heavier than the scattering device 19. However, these problems are solved by the present embodiment, which fixes the scattering device 63 and moves the scattering device 19 along its axis.

Fourth Embodiment

A fourth embodiment of the present invention will now be described. The particle beam therapy system according to the fourth embodiment is such that the irradiation apparatus 15B according to the third embodiment is replaced by a scatterer type, second irradiation apparatus. The particle beam therapy system according to the present embodiment does not include the drive controller 58. The second irradiation apparatus differs from the irradiation apparatus 15B in that a scattering device 19 is mounted in a casing 16 via a support member 67 in a stationary manner while a range adjustment device 20 is mounted in the casing 16 and rendered movable in the direction of the beam axis 14. The drive device for moving the range adjustment device 20 in the direction of the beam axis 14 is configured the same as the drive device (an AC servomotor 65 and a ball screw 66) for moving the scattering device 19 in the irradiation apparatus 15B in that direction, and mounted in the casing 16.

As is the case with third embodiment, an irradiation controller 54 selects a scatterer thickness and absorber thickness. A memory 55 stores RS position information instead of the "SC+RS position" information, which is shown as part of the irradiation condition information shown in Table 1. The stored RS position information is the positional information about the range adjustment device 20. The RS position is a position that is based on the first reference position for the range adjustment device 20. As is the case with the third embodiment, the drive controller 56 selects a required scatterer and absorber and exercises control so as to move the selected scatterer and absorber to an ion beam passage position. A bolus 22 and a collimator 23 are also mounted in the casing 16.

The irradiation controller 54 outputs the RS position information, which is the first position information, as well as a drive instruction to a drive controller 57. In accordance with the RS position information, the drive controller 57 rotates an AC servomotor in order to move a support member 68 to a specified position along the beam axis 14. After an ion beam is emitted from the rotary irradiation device 10 and incident on the second irradiation apparatus, it sequentially passes through the selected scatterer of the scattering device 19, scattering device 63, Bragg peak spreading device 21, range adjustment device 20, bolus 22, and collimator 23 and then falls on the diseased part 62.

The present embodiment moves the absorber in the direction of ion beam propagation. The radiation dose distribution for the diseased part 62, which results from ion beam scatter changes caused by a selected absorber as described in conjunction with the first embodiment, can therefore be uniformed to a higher degree than a conventional configuration. In addition, the present embodiment improves the ion beam usability and increases the radiation dose rate.

Fifth Embodiment

A fifth embodiment of the present invention will now be described. The particle beam therapy system according to the fifth embodiment is such that the irradiation apparatus 15B according to the third embodiment is replaced by a scatterer type, third irradiation apparatus. The particle beam therapy system according to the present embodiment does not include the drive controller 57. The third irradiation apparatus differs from irradiation apparatus 15B in that a scattering device 19 is mounted in a casing 16 via a support member 67 in a stationary manner while a SOBP device 21 is mounted in a casing 16 and rendered movable in the direction of the beam axis 14. The present embodiment is equal to the first embodiment in that the SOBP device 21 is movable in the direction of the beam axis 14.

As is the case with the third embodiment, a irradiation controller 54 selects a scatterer thickness and absorber thickness. A memory 55 stores the irradiation condition information shown in Table 1 excluding the "SC+RS position" information and also stores the irradiation condition information shown in Table 2. As is the case with the third embodiment, a drive controller 56 selects a required scatterer and absorber and exercises control so as to move the selected scatterer and absorber to an ion beam passage position. A bolus 22 and a collimator 23 are also mounted in the casing 16.

The irradiation controller 54 outputs the positional information about the SOBP device 21, which is the second position information, as well as a drive instruction to a drive controller 58. In accordance with the second position information, the drive controller 58 rotates an AC servomotor in order to move a support member 30 to a specified position along the beam axis 14. After an ion beam is emitted from a rotary irradiation device 10 and incident on the third irradiation apparatus, it falls on a diseased part 62 in the same manner as described in conjunction with the fourth embodiment.

The present embodiment moves the SOBP device 21 in the direction of ion beam propagation. Consequently, as described in conjunction with the first embodiment, the present embodiment makes it possible to adjust the changes in the radiation dose distribution for the diseased part 62, which arise depending on the SOBP device 21 that is set. As a result, the present embodiment provides a higher degree of uniformity of radiation dose distribution for the diseased part 62 than a conventional configuration. The present embodiment also improves the ion beam usability and increases the radiation dose rate.

The third to fifth embodiments move one of scattering device 19, range adjustment device 20, and SOBP device 21, all of which are moved by the first embodiment. Therefore, the third to fifth embodiments are inferior to the first embodiment in the capability for adjusting the degree of uniformity of radiation dose distribution for the diseased part 62, but provide a higher degree of radiation dose distribution uniformity than a conventional configuration.

An alternative configuration may be employed for the third embodiment so that at least one of the range adjustment device 20 and SOBP device 21 is rendered movable in addition to the scattering device 19, which is movable. When the drive device for the range adjustment device 20 is mounted in the casing 16, the range adjustment device 20 can move along the beam axis 14. When the drive device for the SOBP device 21 is mounted in the casing 16 as shown in FIG. 2, the SOBP device 21 can move along the beam axis 14. When, for instance, the range adjustment device 20 and SOBP device 21 are rendered movable in addition to the scattering device 19, the degree of uniformity of radiation dose distribution for the diseased part 62 is higher than that provided by the third embodiment and equal to that provided by the first embodiment. Further, an alternative configuration may be employed for the fourth embodiment so that the SOBP device 21 is rendered movable in addition to the range adjustment device 20, which is movable. This alternative configuration can be achieved by mounting the drive device for the above SOBP device 21 in the casing 16.

Sixth Embodiment

Figure 12:
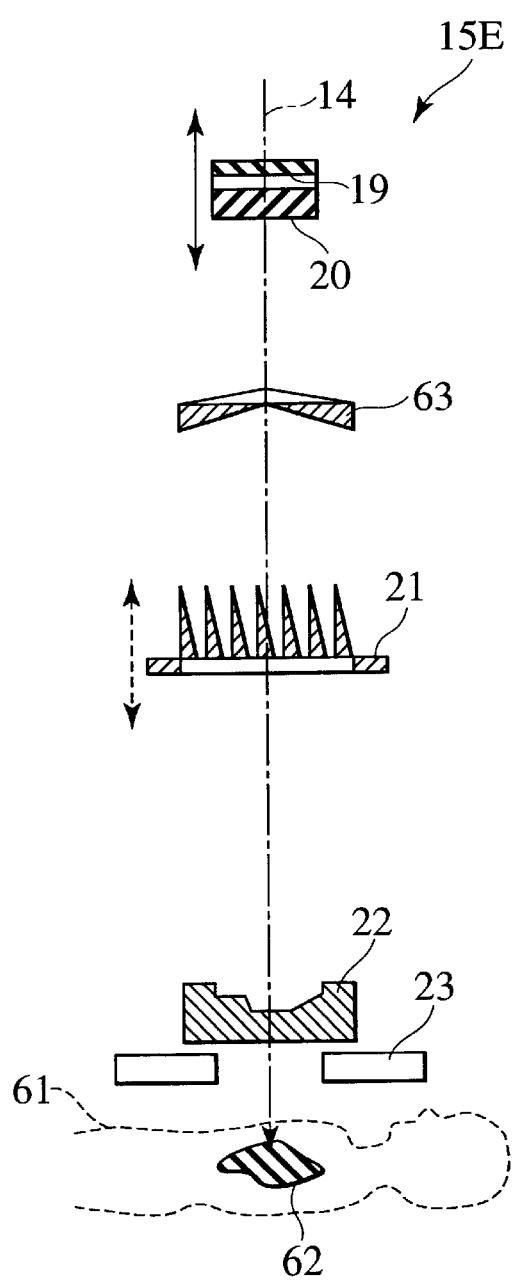
FIG. 12 illustrates the configuration of an irradiation apparatus for use with a particle beam therapy system in accordance with a sixth embodiment of the present invention.

A sixth embodiment of the present invention will now be described. The particle beam therapy system according to the sixth embodiment is such that the irradiation apparatus 15 according to the first embodiment is replaced by an irradiation apparatus 15E, which is shown in FIG. 12. The irradiation apparatus 1SE differs from the irradiation apparatus 15B in that a combination of a scattering device 19 and a range adjustment device 20, which are integral with each other as described in conjunction with the first embodiment, is positioned upstream of a scattering device 63, which is the second scatterer, and that the scattering device 19, range adjustment device 20, and SOBP device 21 are movable along the beam axis 14. A drive device for moving the integral combination of the scattering device 19 and range adjustment device 20 along the beam axis 14 is configured the same as its drive device shown in FIG. 1. A drive device for moving the SOBP device 21 along the beam axis 14 is configured the same as its drive device shown in FIG. 1.

An irradiation controller 54 and drive controllers 56, 57, 58 for the present embodiment function the same as the counterparts for the first embodiment. The ion beam incident on the irradiation apparatus 15E passes through internal components and falls on a diseased part 62.

Since the present embodiment moves the scattering device 19, range adjustment device 20, and SOBP device 21 along the beam axis 14, it can uniform the radiation dose distribution for the diseased part 62 as is the case with the first embodiment. In the present embodiment, the integral combination of the scattering device 19 and range adjustment device 20 is positioned upstream of a scattering device 63. Therefore, even when the amount of range adjustment is increased by a selected absorber, the present embodiment can increase the effective radiation source distance and decrease the effective radiation source size. Consequently, the radiation dose distribution penumbra (half shadow) beyond the diseased part decreases. Further, the size of the ion beam incident on the range adjustment device 20 decreases, thereby making it possible to downsize the range adjustment device 20.

When the range adjustment device 10 is positioned upstream of the scattering device 63, which is the second scatterer, the amount of radiation dose distribution variation increases due to range adjustments. However, the present embodiment can move the scattering device 19 and range adjustment device 20 in the direction of the beam axis 14, thereby making it possible to adjust the amount of radiation dose distribution variation. Since the scattering device 19 and range adjustment device 20 are integral with each other, the amount of their travel in the direction of the beam axis 14 can be reduced. When the amount of ion beam energy loss in the range adjustment device 20 increases (when a thick absorber is selected), the amount of ion beam scattering in the scattering device 63 increases as well. Therefore, when the scattering device 19 and range adjustment device 20 move, the amount of variation in the radiation dose distribution for the diseased part 62 can be reduced without regard to the amount of ion beam range adjustment by the absorber.

An alternative configuration may be employed for the present embodiment so that either the integral combination of the scattering device 19 and range adjustment device 20 or the SOBP device 21 is immovable along the beam axis 14. When the integral combination of the scattering device 19 and range adjustment device 20 is immovable, inserting an absorber into the ion beam passage region causes an increase in the amount of ion beam incidence on the outer region of the scattering device 63. However, as the energy is decreased by the absorber insertion, the degree of ion beam scattering at the position of scattering device 63 becomes higher than when no absorber is inserted.

Another embodiment of a wobbling type irradiation apparatus will now be described. The irradiation apparatus according to the present embodiment, which is referred to as the Type A irradiation apparatus, is configured so that the scattering device 63 of the irradiation apparatus 15B (FIG. 11) is replaced by the first scanning magnet 17 and second scanning magnet 18 shown in FIG. 1. A scattering device 19 located upstream of the first scanning magnet 17 can move in the direction of the beam axis 14. A range adjustment device 20 and a SOBP device 21 do not move in the direction of the beam axis 14. In the irradiation apparatus according to the present embodiment, at least one of the range adjustment device 20 and SOBP device 21 may additionally move in the direction of the beam axis 14. Even when the irradiation apparatus is configured as described above, it provides a higher degree of uniformity of radiation dose distribution for a diseased part 62 than a conventional configuration.

Still another embodiment of a wobbling type irradiation apparatus will now be described. The irradiation apparatus according to the present embodiment, which is referred to as the Type B irradiation apparatus, is configured so that the scattering device 19 of the Type A irradiation apparatus is positioned downstream of the second scanning magnet 18 and upstream of a SOBP device 21. In the present embodiment, the scattering device 19 is movable in the direction of the beam axis 14; however, a range adjustment device 20 and the SOBP device 21 are immovable in the direction of the beam axis 14. In the Type B irradiation apparatus, at least one of the range adjustment device 20 and SOBP device 21 may additionally move in the direction of the beam axis 14. Even when the irradiation apparatus is configured as described above, it provides a higher degree of uniformity of radiation dose distribution for a diseased part 62 than a conventional configuration.

Seventh Embodiment

A seventh embodiment of the present invention, which is based on a scanning type irradiation apparatus, will now be described. The particle beam therapy system according to the seventh embodiment is different from the particle beam therapy system shown in FIG. 1 in ion beam scanning control that the scanning magnet controller 36 exercises for the first scanning magnet 17 and second scanning magnet 18.

Ion beam scanning conducted by the present embodiment will now be described in detail. An irradiation controller 54 acquires ion beam scanning condition information (e.g., exciting current patterns shown in FIG. 13A) about scanning of a patient 61 from a memory 55, and outputs it to the scanning magnet controller 36. The ion beam scanning condition information is created when a therapy plan is formulated for the patient 61. In accordance with the exciting current pattern information, the scanning magnet controller 36 controls the currents that are supplied respectively to the first scanning magnet 17 and second scanning magnet 18. The ion beam scanned by the first scanning magnet 17 and second scanning magnet 18 passes through a scattering device 19, a range adjustment device 20, a SOBP device 21, a bolus 22, and a collimator 23, and falls on a diseased part 62. As described in conjunction with the first embodiment, wobbling type ion beam scanning is conducted in accordance with the exciting current patterns for the scanning magnets shown in FIG. 13B.

The employed scanning method provides irradiation while scanning an ion beam within a plurality of regions into which the diseased part 62 is divided (e.g., the diseased part 62 is divided into a plurality of regions in the direction of the in vivo depth). This scanning method can provide ion beam irradiation in accordance with the shape of the diseased part 62, thereby preventing healthy cells neighboring the diseased part 62 from being exposed to the ion beam. When the exciting currents are controlled as indicated by the above-mentioned exciting current patterns shown in FIG. 13A, the ion beam propagates in a fixed direction while zigzagging within a divided region described above. Ion beam scanning is conducted in this manner to complete ion beam irradiation for one divided region. The ion beam energy is varied in order to move the ion beam into the other divided regions, which vary in the depth from the patient body surface.

If a conventional scanning type irradiation apparatus is used for ion beam scanning, a problem arises. More specifically, the ion beam size varies with the ion beam length in the direction of propagation within divided regions or the position in the direction of the in vivo depth. However, the present embodiment can adjust the ion beam size because it moves the scattering device 19 in the direction of the beam axis 14. The present embodiment also moves the range adjustment device 20 in the same direction, thereby making it possible to adjust ion beam size changes arising out of ion beam scatter changes that are caused when the range is adjusted by a selected absorber. Further, the present embodiment moves an SOBP device 21, thereby making it possible to adjust ion beam changes that are caused by a selected SOBP device 21. As described above, the present embodiment can adjust the ion beam size. Consequently, the present embodiment solves the aforementioned problem in which the ion beam size varies with the ion beam length in the direction of propagation within the divided regions or the position in the direction of the in vivo depth. The present embodiment can easily adjust the ion beam size by moving the scattering device 19, range adjustment device 20, and SOBP device 21 along the beam axis 14.

Eighth Embodiment

An eighth embodiment of the present invention, which is based on a scanning type irradiation apparatus, will now be described. The particle beam therapy system according to the eighth embodiment is structured the same as the particle beam therapy system shown in FIG. 1 and provided with the irradiation apparatus 15 shown in FIG. 2. In the present embodiment, the scanning magnet controller 36 exercises ion beam scanning control over the first scanning magnet 17 and second scanning magnet 18 in a manner other than used by the first and seventh embodiments. As is the case with the seventh embodiment, the present embodiment irradiates divided regions of the diseased part 62 with an ion beam.

The irradiation controller 54 reads the ion beam scanning condition information about scanning of the patient 61 from the memory 55, and outputs it to the scanning magnet controller 36. The ion beam scanning condition information consists of the exciting current patterns of the first scanning magnet 17 and second scanning magnet 18 shown in FIG. 13C. In accordance with the exciting current pattern information, the scanning magnet controller 36 controls the exciting currents that are supplied respectively to the first scanning magnet 17 and second scanning magnet 18. The exciting current patterns shown in FIG. 13C are obtained by combining the scanning type exciting current patterns shown in FIG. 13A with the wobbling type exciting current patterns shown in FIG. 13B.

The ion beam scanned by the first scanning magnet 17 and second scanning magnet 18 passes through the scattering device 19, range adjustment device 20, SOBP device 21, bolus 22, and collimator 23, and falls on the diseased part 62.

Figure 13C:
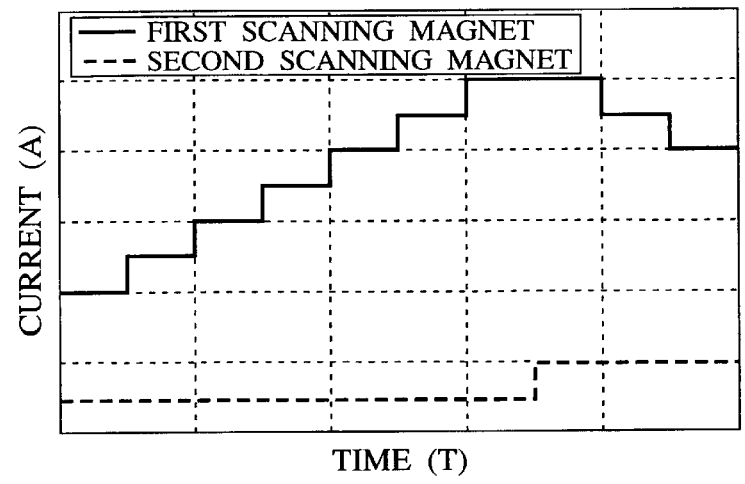
FIG. 13C is a graph that relates to scanning in an eighth embodiment and illustrates the exciting current patterns for scanning magnets of an irradiation apparatus.

The present embodiment controls the scanning magnets in accordance with the exciting current patterns shown in FIG. 13C. Therefore, it solves the problem that occurs with the seventh embodiment in which the ion beam size varies, for instance, with the ion beam length in the direction of propagation. That is, the ion beam size remains unchanged even if there is a change in the ion beam length in the direction of ion beam propagation within the divided regions or in the position in the direction of the in vivo depth. In reality, the ion beam shape is similar to that of Gauss distribution. If a circular orbit is drawn by means of wobbling, the ion beam shape represents a circular integral of a distribution shape similar to that of Gauss distribution. However, if the circular orbit for scanning is small relative to the amount of ion beam scattering, it is impossible to presume that the ion beam shape is similar to that of Gauss distribution. More specifically, the scanning magnet controller 36 controls the exciting currents to be supplied to the first scanning magnet 17 and second scanning magnet 18 in such a manner as to make the wobbling pattern (chronological changes in the current value to be applied to a wobbling magnet) larger for a region irradiated with a small beam and make the wobbling pattern smaller for a region irradiated with a large beam. When the present embodiment is applied to raster scanning, an ion beam scan is conducted while drawing a spiral orbit. When the present embodiment is applied to voxel scanning, irradiation takes place in such a manner that each ion beam draws a circular orbit at a fixed position. The present embodiment can adjust ion beam size variations as is the case with the seventh embodiment.

If an alternative configuration is employed for the seventh or eighth embodiment so that one or two of the scattering device 19, range adjustment device 20, and SOBP device 21 are moved along the beam axis 14 instead of moving all of them along the beam axis 14, the result is inferior to that is obtained when all of them are moved. However, such an alternative configuration inhibits ion beam size variations to a higher degree than a conventional scanning method.

In embodiments other than the first embodiment and where the first and second scanning magnets are provided, the scanning magnet controller 36 can control the exciting currents to be supplied to the first and second scanning magnets in accordance with the exciting current patterns described in conjunction with the seventh and eighth embodiments.

All the embodiments described above relate to a particle beam therapy system that includes a synchrotron. However, the irradiation apparatuses described in conjunction with the foregoing embodiments are also applicable to a particle beam therapy system that includes a cyclotron. The particle beam therapy system containing a cyclotron can obtain a desired ion beam range by preselecting an appropriate bottom thickness for the bolus 22 instead of using the range adjustment device.

All the foregoing embodiments are applicable to a material irradiation system that contains a charged particle beam generation apparatus and irradiation apparatus and exposes materials to a charged particle beam, a food irradiation system for exposing food to a charged particle beam, and a radioisotope production system based on a charged particle beam.

The present invention enhances the uniformity of radiation dose distribution for the irradiation target that is irradiated with a charged particle beam.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A particle beam irradiation system, comprising:
   a charged particle beam generation apparatus; and
   an irradiation apparatus for exposing an irradiation target to a charged particle beam emitted from the charged particle beam generation apparatus;
   wherein said irradiation apparatus includes a scattering device for increasing the size of said charged particle beam and a Bragg peak spreading device through which said charged particle beam passes; and
   wherein at least one of said scattering device and said Bragg peak spreading device is installed in said irradiation apparatus in such a manner as to be movable in a propagation direction of said charged particle beam.

2. The particle beam irradiation system according to claim 1, further comprising a controller for placing at least one of said scattering device and said Bragg peak spreading device at a position that is in the propagation direction of said charged particle beam and that is determined in accordance with therapy plan information.

3. A particle beam irradiation system, comprising:
   a charged particle beam generation apparatus; and
   an irradiation apparatus for exposing an irradiation target to a charged particle beam emitted from the charged particle beam generation apparatus;
   wherein said irradiation apparatus includes a scattering device for increasing the size of said charged particle beam, a range adjustment device for varying the range of said charged particle beam, and a Bragg peak spreading device through which said charged particle beam passes; and
   wherein at least one of said scattering device, said range adjustment device, and said Bragg peak spreading device is installed in said irradiation apparatus in such a manner as to be movable in a propagation direction of said charged particle beam.

4. The particle beam irradiation system according to claim 3, wherein said scattering device and said range adjustment device are combined together.

5. The particle beam irradiation system according to claim 4, further comprising a drive device for moving a combination of said scattering device and said range adjustment device in said propagation direction and a drive controller for controlling said drive device and controlling an amount of movement of said combination of the scattering device and the range adjustment device.

6. The particle beam irradiation system according to claim 3, further comprising a drive device for moving said scattering device in said propagation direction and a drive controller for controlling said drive device and controlling an amount of movement of said scattering device.

7. The particle beam irradiation system according to claim 3, further comprising a drive device for moving said range adjustment device in said propagation direction and a drive controller for controlling said drive device and controlling an amount of movement of said range adjustment device.

8. The particle beam irradiation system according to claim 3, further comprising a drive device for moving said Bragg peak spreading device in said propagation direction and a drive controller for controlling said drive device and controlling an amount of movement of said Bragg peak spreading device.

9. A particle beam irradiation system, comprising:
a charged particle beam generation apparatus; and
an irradiation apparatus for irradiating an irradiation target with a charged particle beam emitted from the charged particle beam generation apparatus;
wherein said irradiation apparatus includes a beam scanner for scanning said charged particle beam, a scattering device for increasing the size of said charged particle beam, and a Bragg peak spreading device through which said charged particle beam passes; and
wherein at least one of said scattering device and said Bragg peak spreading device is installed in said irradiation apparatus in such a manner as to be movable in a propagation direction of said charged particle beam.

10. The particle beam irradiation system according to claim 9, further comprising a controller for placing at least one of said scattering device and said Bragg peak spreading device at a position that is in the propagation direction of said charged particle beam and that is determined in accordance with therapy plan information.

11. A particle beam irradiation system, comprising:
a charged particle beam generation apparatus; and
an irradiation apparatus for exposing an irradiation target to a charged particle beam emitted from the charged particle beam generation apparatus;
wherein said irradiation apparatus includes a beam scanner for scanning said charged particle beam, a scattering device for increasing the size of said charged particle beam, a range adjustment device for varying the range of said charged particle beam, and a Bragg peak spreading device through which said charged particle beam passes; and
wherein at least one of said scattering device, said range adjustment device, and said Bragg peak spreading device is installed in said irradiation apparatus in such a manner that the device is movable in the propagation direction of said charged particle beam.

12. The particle beam irradiation system according to claim 11, wherein said scattering device and said range adjustment device are combined together.

13. The particle beam irradiation system according to claim 11, further comprising a beam scan controller for controlling said beam scanner and controlling the scan of said charged particle beam to which said irradiation target is exposed.

14. The particle beam irradiation system according to claim 13, wherein said beam scan controller controls said beam scanner so as to scan said charged particle beam in a scanning pattern for a region within said irradiation target.

15. The particle beam irradiation system according to claim 11, wherein a combination of said scattering device and said range adjustment device is installed in said irradiation apparatus in such a manner that the combination is movable in said propagation direction.

16. The particle beam therapy system according to claim 11, wherein a combination of said scattering device and said range adjustment device is positioned upstream of said beam scanner in said propagation direction.

17. The particle beam therapy system according to claim 11, wherein a combination of said scattering device and said range adjustment device is positioned downstream of said beam scanner in said propagation direction.

18. The particle beam therapy system according to claim 11, wherein said Bragg peak spreading device is positioned upstream of said beam scanner in said propagation direction.

19. The particle beam therapy system according to claim 12, comprising a drive device for moving a combination of said scattering device and said range adjustment device in said propagation direction and a drive controller for controlling said drive device and controlling an amount of movement of said combination of the scattering device and the range adjustment device.

20. A particle beam irradiation system, comprising:
a charged particle beam generation apparatus; and
an irradiation apparatus for exposing an irradiation target to a charged particle beam emitted from the charged particle beam generation apparatus,
wherein said irradiation apparatus includes a first scattering device for increasing the size of said charged particle beam, a second scattering device through which said charged particle beam passing through said first scattering device passes, and a Bragg peak spreading device through which said charged particle beam passes; and
wherein at least one of said scattering devices and said Bragg peak spreading device is installed in said irradiation apparatus in such a manner as to be movable in a propagation direction of said charged particle beam.

21. The particle beam irradiation system according to claim 20, further comprising a controller for placing at least one of said scattering devices and said Bragg peak spreading device at a position that is in the propagation direction of said charged particle beam and that is determined in accordance with therapy plan information.

22. A particle beam irradiation system, comprising:
a charged particle beam generation apparatus; and
an irradiation apparatus for exposing an irradiation target to a charged particle beam emitted from the charged particle beam generation apparatus;
wherein said irradiation apparatus includes a first scattering device for increasing the size of said charged particle beam, a second scattering device through which said charged particle beam passing through said first scattering device passes, a range adjustment device for varying the range of said charged particle beam, and a Bragg peak spreading device through which said charged particle beam passes; and
wherein at least one of said scattering devices, said range adjustment device, and said Bragg peak spreading device is installed in said irradiation apparatus in such a manner as to be movable in a propagation direction of said charged particle beam.

23. The particle beam irradiation system according to claim 22, wherein said first scattering device and said range adjustment device are combined together and the resulting combination of said first scattering device and said range adjustment device is positioned upstream of said second scattering device in said propagation direction.

24. The particle beam irradiation system according to claim 23, wherein a combination of said scattering device and said range adjustment device is installed in said irradiation apparatus in such a manner as to be movable in said propagation direction.

* * * * *